(12) United States Patent
Zebala

(10) Patent No.: US 6,569,598 B2
(45) Date of Patent: May 27, 2003

(54) SOLVENT RESISTANT PHOTOSENSITIVE COMPOSITIONS

(75) Inventor: John A. Zebala, Redmond, WA (US)

(73) Assignee: Syntrix Biochip, Inc., Redmond, WA (US)

(*) Notice: Subject to any disclaimer, the term of this patent is extended or adjusted under 35 U.S.C. 154(b) by 105 days.

(21) Appl. No.: 09/836,929

(22) Filed: Apr. 17, 2001

(65) Prior Publication Data

US 2003/0064316 A1 Apr. 3, 2003

Related U.S. Application Data

(63) Continuation of application No. 09/448,271, filed on Nov. 24, 1999, now abandoned.
(60) Provisional application No. 60/110,528, filed on Dec. 1, 1998.

(51) Int. Cl.[7] .......................... G03C 1/73; G03F 7/039; C08G 69/14; C08G 69/26; C08L 77/06
(52) U.S. Cl. .................. 430/270.1; 430/326; 430/906; 525/420; 528/324; 528/332; 528/335
(58) Field of Search .................... 525/420; 528/324, 528/332, 335; 430/270.1, 906, 326

(56) References Cited

U.S. PATENT DOCUMENTS

| | | | |
|---|---|---|---|
| 3,624,033 A | 11/1971 | Steinmann et al. | 260/47 |
| 4,297,479 A | 10/1981 | Rochina et al. | 528/336 |
| 5,089,600 A | 2/1992 | Blackmon et al. | 528/335 |
| 5,202,231 A | 4/1993 | Drmanac et al. | 435/6 |
| 5,252,464 A | 10/1993 | Andersen | 435/68.1 |
| 5,445,934 A | 8/1995 | Fodor et al. | 435/6 |
| 5,700,637 A | 12/1997 | Southern | 435/6 |
| 5,795,716 A | 8/1998 | Chee et al. | 435/6 |
| 5,800,992 A | 9/1998 | Fodor et al. | 435/6 |
| 6,103,862 A | 8/2000 | Noh | 528/332 |

OTHER PUBLICATIONS

Chaudhuri et al., "Thermal Properties of Wholly Aromatic Polyamides," *J. Polymer Science Polymer Chemistry Edition* 18 (10):2949–2958, 1980.
Kim et al., "The Synthesis of a Precursor of Polybenimidazole (PBI) and Blends with Polyamic Acid (PAA)," *J. Polymer Science: Part A: Polymer Chemistry* 31 (13):3167–3180, 1993.
Lozano et al., "Synthesis and Polycondensation of Novel Nitro-aromatic Monomers: 4,4'-Diamino-3'-Nitrobenzanilide," *J. Polymer Science: Part A: Polymer Chemistry* 33 (5):873–877, 1995.
MacDonald et al., "Poly(N-Alkyl-o-Nitroamides) a New Class of Photosensitive Polymers," *Organic Coatings and Plastics Chemistry* 43:264–267, 1980.
Oh et al., "The Effect of the Bridge Group of the Thermal Stability of Nitro-Substituted Aromatic Polyamides," *Polymers for Advanced Technologies* 4 (10):577–582, 1993.
Chemical Abstracts, Accession No. 97:47069 CA, Aug. 9, 1982.
Chemical Abstracts, Accession No. 96:226485 CA, Jun. 28, 1982.

*Primary Examiner*—Rosemary Ashton
*Assistant Examiner*—Sin J. Lee
(74) *Attorney, Agent, or Firm*—Charles R. Haymond

(57) ABSTRACT

Photoresist compositions and methods are provided for preparing photoresist films that are stable and impermeable to a broad range of organic solvents. Photoresist films provided herein may be photopatterned by selectively applying light, and may be stripped from a surface using unreactive agents. Photopatterned films may be used, for example, to selectively direct organic reagents to a solid support for the purpose of performing regionally selective solid-phase chemical synthesis with micron-scale resolution.

48 Claims, No Drawings

SOLVENT RESISTANT PHOTOSENSITIVE COMPOSITIONS

CROSS REFERENCE TO RELATED APPLICATION

This application is a continuation of U.S. patent application Ser. No. 09/448,271, filed Nov. 24, 1999, now abandoned, which claims the benefit of U.S. Provisional Patent Application No. 60/110,528, filed Dec. 1, 1998.

TECHNICAL FIELD

The present invention relates generally to positive photoresist compositions. The invention is more particularly related to photoactive poly(N-alkyl-o-nitroamides), which may be used to prepare photosensitive compositions that yield en dry photoresist films that are resistant to a broad range of organic solvents.

BACKGROUND OF THE INVENTION

Receptor-ligand interactions are critical components of many fundamental biological processes. Such interactions involve specific binding of a macromolecule receptor (e.g., enzyme, cell-surface protein, antibody or oligonucleotide) to a particular ligand molecule. Receptor-ligand binding may affect any of a variety of intercellular and intracellular processes in an organism, such as signal transduction, gene expression, immune responses or cell adhesion. An improved understanding of receptor-ligand interactions is necessary for many areas of research in the life sciences, as well as for the development of agents that modulate such interactions for therapeutic and other applications.

Miniaturized ligand-arrays, formed using microfabrication and solid-phase chemical synthesis on substantially planar supports, have been used to facilitate the study of receptor-ligand interactions (for representative examples, see Fodor et al., Science (1991) 251:767; Pease et al., Proc. Natl. Acad. Sci. USA 91:5022, 1994; Pirrung et al., U.S. Pat. No. 5,405,783; Fodor et al., U.S. Pat. No. 5,445,934; Pirrung et al., U.S. Pat. No. 5,143,854; Fodor et al., U.S. Pat. No. 5,424,186 and Fodor et al., U.S. Pat. No. 5,510,270; Chee et al., Science (1996) 274:610 and Brennan, U.S. Pat. No. 5,474,796). Contacting a ligand array with labeled receptor allows many ligands to be simultaneously screened for receptor binding. The location of bound receptor on the array is determined by detecting photons or radioactivity. However, the surface density of ligand is often low, resulting in the need for costly imaging equipment and long image acquisition times. Drug discovery efforts have been further hampered by low ligand surface density, since many functional assays require higher ligand concentrations to identify drug leads.

One approach to increasing surface density of ligands involves immobilizing ligands on an array of polyacrylamide pads using microfabrication techniques (see Guschin et al., Anal. Biochem. 250:203, 1997 and Yershov et al., Proc. Natl. Acad. Sci. USA 93:4913, 1996). Such an approach increases the surface density of the ligands, but places a size restriction on diffusion into the polymer that many receptors exceed. Furthermore, such polymeric supports may not be compatible with solid-phase chemical synthesis, which requires adequate swelling and solvation of a polymeric matrix in order to achieve efficient mass transfer of reagents. Further, although this polymer can be photopatterned (i.e., multiple discrete pads may be generated by a process involving exposure to irradiation), the photosensitivity is severely limited, requiring 30 minutes of illumination. Such a low throughput is inadequate for mass production.

Photopatterned barriers with improved photosensitivity and other properties could potentially permit the preparation of higher density arrays, using solid-phase synthesis and a series of photopatterned barrier layers. Such barrier layers could allow applied reagents to react with surface-attached molecules only in predefined regions. Within such a procedure, however, a barrier layer must meet several criteria. First, the barrier layer should maintain integrity and impermeability while in contact with reagents solubilized in a wide variety of solvents. Second, irradiated regions of the barrier layer must undergo a photochemical reaction that is substantially inert with respect to the surface-attached molecules in contact with the layer. Third, removal of the barrier layer must be accomplished with a stripping solution that does not react with the surface-attached molecules. Finally, the barrier layer must be photopatterned with light having a wavelength larger than about 300 nm in order to avoid direct photodegradation of the surface-attached molecules.

Although numerous negative and positive photoresist compositions have been described, compositions that meet the above criteria are not currently available. For example, negative photoresists containing cinnamate, chalcone, coumarin, diphenylcyclopropene, bis-azide, and other such similar groups function by light-induced cross-link formation [see Desk Reference of Functional Polymers: Synthesis and Applications, edited by Reza Arshady, (1997), American Chemical Society, Washington, DC., Chapters 2.1 and 2.3]. Although the irradiated films are insoluble in numerous solvents, the photoreactions leading to cross-linking also react non-specifically with other molecules in contact with the photoresist. Similarly, harsh stripping agents required to remove the cross-linked photoresist film will degrade other molecules indiscriminately. Such cross-linking and stripping reactions are incompatible with photoresist directed solid-phase synthesis.

A further problem encountered with cross-linked photoresists relates to swelling of irradiated regions in a variety of solvents. In order to generate an image, the unexposed regions of a negative photoresist must be removed by solubilization with a suitable solvent. Any solvent that will dissolve the uncross-linked material will also interact with the cross-linked regions to produce a solvated and swollen-state. Though the irradiated regions maintain their overall integrity, swelling results in image distortion, reduced resolution, and permeability of reagents such that the photoresist fails to provide a barrier. Such difficulties are avoided in photoresists that employ a radiation-induced solubility differential resulting from changes in chemical (e.g., a polarity change) rather than physical (e.g., cross-linking) properties.

Positive photoresists containing a phenolic polymer and a diazoquinone are well known in the art, and have been used extensively in microelectronic manufacturing [see U.S. Pat. Nos. Steinhoff et al., U.S. Pat. No. 3,402,044; Moore, U.S. Pat. No. 2,797,213; Endermann et al., U.S. Pat. No. 3,148,983; Schmidt, U.S. Pat. No. 3,046,118; Neugebauer et al., U.S. Pat. No. 3,201,239; Sus, U.S. Pat. No. 3,046,120; Fritz et al., U.S. Pat. No. 3,184,310; Borden, U.S. Pat. No. 3,567,453; and Pampaione, U.S. Pat. No. 4,550,069]. Such positive photoresists employ a radiation-induced polarity change that transforms the diazoquinone from a hydrophobic molecule to a carboxylic acid. Selective dissolution of irradiated regions ensues upon contact with an aqueous alkaline developer. Although swelling by the developer is avoided, diazoquinone photoresists are unsuitable as barrier layers for reagents during solid-phase synthesis since they are soluble in a variety of organic solvents.

Other positive photoresists have been developed for the microelectronic industry based on polyamides, polyimides, and polyamic acids. In all cases, the art teaches that it is desirable to prepare such compositions so they are soluble in conventional process solvents. For example, polyamide photoresists and polyimides have been described with modifications that intentionally provide a broad solubility profile to these polymers [see Mueller and Khanna, U.S. Pat. No. 4,927,736; Kwong et al., U.S. Pat. No. 5,114,826 and Flaim et al., U.S. Pat. No. 5,281,690]. In contrast, photoresist directed solid-phase synthesis requires a broad insolubility profile so as to provide a film that maintains integrity and impermeability while in contact with a myriad of solvents.

Efforts to develop both positive and negative photoresists for microelectronics have also been directed toward compositions that are reactive to very short wavelengths of light or electron beams [see *Desk Reference of Functional Polymers: Synthesis and Applications*, edited by Reza Arshady, (1997), American Chemical Society, Washington, DC., Chapters 2.3 and 2.4]. The wavelength of light that a photoresist is reactive to determines the minimum possible feature size. Accordingly, efforts to increase the number of microelectronic components on silicon chips have focused on photoresists reactive to the deep ultraviolet and x-ray portions of the electromagnetic spectrum. However, many molecules absorb such high energy light making it incompatible with a stable array of surface-attached molecules made by solid-phase synthesis.

It is known that a substantially inert photoreaction is provided by the intramolecular photo-oxidation of o-nitrobenzyl and N-alkyl-o-nitroanilide groups [see review by Pillai, Synthesis 1980 (1980) p. 1]. Although positive photoresists have been described that incorporate these chemistries, the photoresists have broad solubility characteristics [see Kubota et al., J. Appl. Polymer Sci.: Polymer Chem. Ed. (1987) 33:1763; Reichmanis et al., J. Appl. Polymer Sci.: Polymer Chem. Ed. (1983) 21:1075; Petropoulos, J. Appl. Polymer Sci.: Polymer Chem. Ed. (1977) 15:1637; Iizawa et al., J. Polymer Sci.: Part A: Polymer Chem. (1991) 29:1875; and MacDonald and Willson, in: *Polymeric Materials for Electronic Applications*, ACS Symp. Ser. 184, American Chemical Society, Washington, DC, edited by MacDonald et al., (1982), p. 73]. These disclosures provide no teaching regarding the production of solvent-resistant photosensitive compositions based on such o-nitrobenzyl or N-alkyl-o-nitroanilide chemistries.

Accordingly, there is a need in the art for a photosensitive composition capable of acting as a patterned barrier layer during solid-phase synthesis of compounds on a support surface. The present invention fulfills this need and further provides other related advantages.

SUMMARY OF THE INVENTION

Briefly stated, the present invention provides photoactive polyamide derivatives and compositions comprising such derivatives. Within certain aspects, a photoactive polyamide derivative comprises a plurality of repeating units represented by the formula:

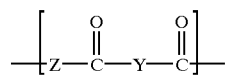

wherein Z in 20 to 100 percent of the plurality of repeating units comprises a divatent radical represented by the formula:

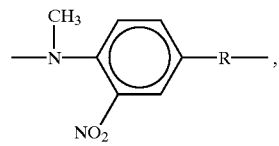

wherein R is a divalent radical; wherein Z in the balance of the plurality of repeating units comprises a divalent radical represented by the formula:

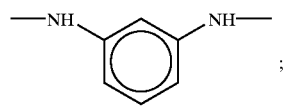

and wherein Y in 10 to 100 percent of the plurality of repeating units comprises an isophthaloyl radical, and Y in the balance of the plurality of repeating units comprises a terephthaloyl radical. Within certain embodiments of the above polyamide derivatives, R is a divalent radical represented by one of the formulas:

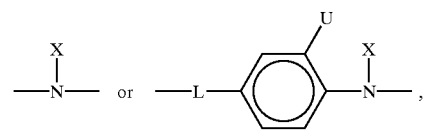

wherein X is H or $CH_3$; L is selected from the group consisting of direct link, O, $CH_2$, $N(CH_3)$, $C(CH_3)_2$, $C(CF_3)_2$, $SO_2$, CO, CONH, $O(C_6H_4)_2$, S, $C(C_6H_5)_2$ $C(CF_3)(C_6H_5)$; and U is selected from the group consisting of H, $NO_2$ and $CH_3$. Within other such derivatives, R is NH. Photoactive polyamide derivatives provided herein preferably have a number average degree of polymerization that is greater than 15, 20, 50 or 100. Within certain embodiments, the polyamide derivative is terminated by a monovalent organic group, such as a group represented by one of the formulas:

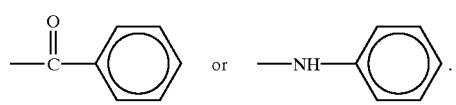

Within certain embodiments, Z in 20 to 50 percent of the plurality of repeating units is a divalent radical represented by the formula:

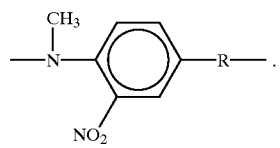

The present invention further provides photosensitive resin compositions, comprising one or more photoactive polyamide as described above, in combination with a solvent. Optionally, such compositions may further comprise one or more photoinactive polyamides, wherein such photoactive polyamide derivative(s) and the photoinactive polyamide(s) are combined to form a substantially homogeneous blend. Certain photoinactive polyamides are formed by the condensation of meta-phenylenediamine with isophthaloyl chloride and terephthaloyl chloride.

Within further aspects, photoactive polyamide derivatives are provided that are the product of the condensation of a diamine mixture with a diacid chloride mixture, wherein the diamine mixture comprises 20 to 50 mole percent of $N^1$-methyl-2-nitro-p-phenylenediamine, with the balance 1,3-phenylenediamine, and wherein the diacid chloride mixture comprises 10 to 100 mole percent of isophthaloyl chloride, with the balance terephthaloyl chloride.

Within other aspects, photoactive polyamide derivatives are provided that are the product of the condensation of a diacid chloride mixture with a diamine mixture, wherein the diacid chloride mixture comprises 10 to 100 mole percent of isophthaloyl chloride, with the balance terephthaloyl chloride, and wherein the diamine mixture comprises 20 to 50 mole percent of an N-alkyl-2-nitro diamine, with the balance 1,3-phenylenediamine, wherein the N-alkyl-2-nitro diamine is:

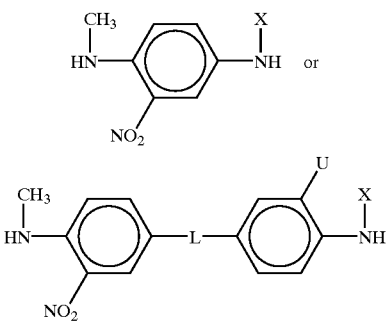

wherein X is H or $CH_3$; L is selected from the group consisting of direct link, O, $CH_2$, $N(CH_3)$, $C(CH_3)_2$, $C(CF_3)_2$, $SO_2$, CO, CONH, $O(C_6H_4)_2$, S, $C(C_6H_5)_2$, $C(CF_3)$ $(C_6H_5)$; and U is selected from the group consisting of H, $NO_2$ and $CH_3$. Within such polyamide derivatives, the N-alkyl-2-nitro diamine may be, for example, $N^1$-methyl-2-nitro-p-phenylenediamine or 3,3'-dinitro-4,4'-di-N-methylaminodiphenyl ether. Preferably, the mole ratio of the diacid chloride mixture to the diamine mixture ranges from 0.909 to 1.100. Within certain embodiments, the diacid chloride mixture condenses with at least 80% of the N-alkyl-2-nitro diamine before condensing with the 1,3-phenylenediamine. Photoactive polyamide derivatives may be terminated with, for example, benzoyl chloride or aniline.

Within further aspects, the present invention provides photosensitive compositions, comprising a photoactive polyamide as described above, in combination with a solvent. Such a composition may further comprise a photoinactive polyamide, such as a polyamide that is the product of condensing meta-phenylenediamine with isophthaloyl chloride and terephthaloyl chloride, wherein the diamine mixture comprises 50 to 100 mole percent of the N-alkyl-2-nitro diamine with the balance 1,3-phenylenediamine.

Within further apsects, photoactive polyamide derivatives are provided that comprise a plurality of repeating units represented by the general formula:

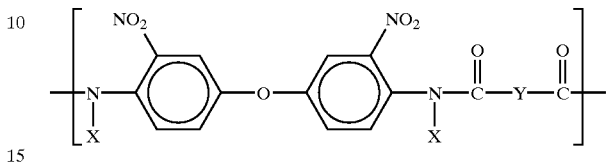

wherein 10 to 100 percent of X radicals are methyl radicals, and wherein the balance of X radicals are H radicals; and wherein 0 to 50 percent of Y radicals are isophthaloyl radicals, with the balance of Y radicals terephthaloyl radicals. Within certain embodiments, such photoactive polyamide derivatives have a number average degree of polymerization that is greater than 15, 20, 50 or 100. Such polyamide derivatives may be terminated by a monovalent organic group, such as a group represented by one of the formulas:

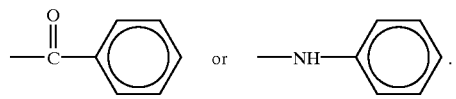

The present invention further provides, within other aspects, photosensitive compositions, comprising a photoactive polyamide as described above, in combination with a solvent.

Within other aspects, methods are provided for producing a photoactive polyamide, comprising the sequential steps of: (a) condensing a diacid chloride mixture with 3,3'-dinitro-4,4'-diaminodiphenyl ether to form a photoinactive polyamide, wherein the diacid chloride mixture comprises from 0 to 50 mole percent of isophthaloyl chloride, with the balance terephthaloyl chloride; and (b) alkylating the photoinactive polyamide with methyl radicals at 10 to 100 mole percent of amide nitrogens; and therefrom generating a photoactive polyamide. The mole ratio of the diacid chloride mixture to 3,3'-dinitro-4,4'-diaminodiphenyl ether may, within certain embodiments, range from 0.909 to 1.100. In some embodiments, the photoinactive polyamide is terminated with benzoyl chloride or aniline.

Within further aspects, the present invention provides photoactive polyamide derivatives having a plurality of repeating units represented by the general formula:

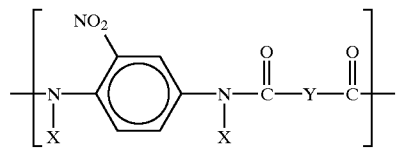

wherein 10 to 50 percent of X radicals are methyl radicals and the balance of X radicals are H radicals, and wherein 20 to 100 percent of Y radicals are isophthaloyl radicals, and the balance of Y radicals are terephthaloyl radicals. Within certain embodiments, such polyamide derivatives have a number average degree of polymerization that is greater than 15, 20, 50 or 100. Such photoactive polyamide derivatives may be terminated by a monovalent organic group, such as a group represented by one of the formulas:

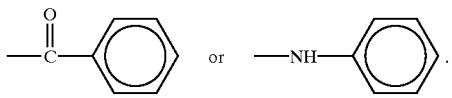

The present invention further provides photosensitive compositions comprising a photoactive polyamide as described above, in combination with a solvent.

Methods are further provided, within other aspects, for producing a photoactive polyamide, comprising the sequential steps of: (a) condensing a diacid chloride mixture with 2-nitro-p-phenylenediamine to form a photoinactive polyamide, wherein the diacid chloride mixture comprises from 0 to 50 mole percent of isophthaloyl chloride, with the balance terephthaloyl chloride; and (b) alkylating the photoinactive polyamide with methyl radicals at 10 to 100 mole percent of amide nitrogens; and therefrom generating a photoactive polyamide. The mole ratio of the diacid chloride mixture to 2-nitro-p-phenylenediamine may range, for example, from 0.909 to 1.100. In certain embodiments, the photoinactive polyamide is terminated with benzoyl chloride or aniline.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

As noted above, the present invention is generally directed to photosensitive compositions that yield dry photoresist films that are stable and impermeable to a broad range of organic solvents. The dry films may be photopatterned by selectively applying light. Using photolithography, it is possible to mask light to relatively small and precisely known locations with exemplary reproducibility and dimensional control, consistent with the production of patterned films with micron-scale resolution. Photopatterned films as provided herein may be used, for example, to selectively direct organic reagents to a solid-support for the purpose of performing regionally selective solid-phase chemical synthesis with micron-scale resolution. Photopatterned films as provided herein have additional advantages, including reactivity to light with a wavelength greater than about 300 nm and solid-state photochemistry that is substantially inert with respect to other molecules in contact with the film. Photoresist layers may further be removed from a substrate using substantially unreactive stripping solutions.

The compositions provided herein generally comprise one or more photoactive polyamide derivatives contairijg at least a portion of polymeric repeats bearing the following photolabile N-alkyl-o-nitroanilide likage:

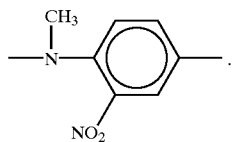

The present invention is based, in part, on the discovery that dry films generated from such compounds are resistant to numerous solvents. It is also a discovery of the instant invention that irradiated regions of such films may be selectively solubilized by non-aqueous developers comprising mixtures of solvents bearing alcohol, amino, ketone, and amide moieties. Such compositions generally undergo a solid-state photochemical reaction upon radiation with 365 nm light, which is substantially inert with respect to other molecules in contact with the photochemical reaction Irradiated regions may be selectively solubilized by substantially inert developer compositions resulting in a patterned photoresist film. In preferred embodiments, the patterned photoresist film serves as a patterned barrier to subsequently applied reagents, allowing such reagents to contact and react with surface-attached molecules only in irradiated regions. Such applications are described in detail in copending application entitled, "Method and Composition For Performing an Array of Chemical Reactions onDa Support Surface" (U.S. Application No. 09/326,479).

GLOSSARY

Prior to setting forth the invention in detail, it may be helpful to an understanding thereof to set forth definitions of certain terms that will be used hereinafter.

A "barrier layer" is a layer of photoresist that prevents detectable contact of a reagent on one side of the layer with a molecule on the other side over a time required for a particular reaction. In other words, a reagent that reacts in a detectable manner with a molecule when the two are combined in solution should not react detectably when separated from the molecule by a barrier layer. In some embodiments the barrier layer will be absolute, preventing detectable contact independent of time. Absolute barrier layers are preferably 0.1 to 20 microns thick, and more preferably 1 to 3 microns thick. In other embodiments the barrier layer will provide a relative diffusion barrier that prevents detectable contact over a specified time interval and specified barrier thickness. In the case of a relative diffusion barrier, a suitable barrier thickness will be determined empirically taking into account the required time of the reaction. In general, the barrier thickness and time interval are directly proportional to one another. That is, reactions requiring longer time intervals will require thicker barrier layers.

A photoresist layer is "continuous" if virtually no straight-line penetrable discontinuities or gaps are detectable in the coating. In other words, such discontinuities or gaps should make up less than 30% of the layer, as detected using, for example, standard microscopy, phase-contrast microscopy, and fluorescence microscopy. It will be apparent that a layer need be continuous only over regions where such coating is necessary for subsequent use. Any number of discontinuities and gaps can exist in other regions.

A layer of photoresist is said to "cover" molecules attached to a surface if the layer forms a continuous coating that is at least 0.1 micron thick.

Exposure of a photoresist to a "developer" may refer to any treatment that dissolves an irradiated portion of a positive photoresist or an unirradiated portion of a negative photoresist, permitting selective removal of the dissolved regions. A developer may be a liquid or gas composition. Certain preferred developers comprise a non-aqueous mixture of solvents containing various ratios of ketone, amino, hydroxyl and amide moieties. Alternatively, a developer may be irradiation. A photoresist is said to be exposed to developer if a developer composition is contacted with the photoresist, or if irradiation is targeted to the photoresist, such that the photoresist is substantially removed in a specific region.

A "discrete known region" is a localized area of a surface on which a substantially pure group of compounds is, was, or is intended to be attached. Such regions do not overlap. A discrete known region may have any convenient shape including circular, rectangular, elliptical, etc., and may be of any size, such as 0.25 to $10^6$ square microns.

"Irradiation" refers to the application of radiation to a target. The amount of irradiation depends on the desired result of the irradiation. In general, irradiation is sufficient to achieve a desired chemical modification on an irradiated molecule. For example, irradiation of a positive photoresist layer is sufficient to permit substantial removal of photoresist from irradiated regions.

"Mask" refers to a substantially transparent support material with substantially opaque regions in a precise pattern where it is desired that light be blocked when one side of the mask is illuminated. In some embodiments the substantially opaque regions are derived through a photographic process using a photoplotting device (e.g., as in masks commonly used in printed circuit board manufacturing). In other embodiments the mask is derived from a substantially transparent support material coated with a substantially opaque material which is photoablated by a narrowly focused laser producing precisely defined transparent regions (e.g., chrome on glass masks). The differential between the intensity of light transmitted by substantially transparent and substantially opaque regions as a percentage of the intensity of light transmitted by substantially transparent regions should be greater than 75%, more preferably greater than 90%, and most preferably greater than 99%.

"Microfabrication" refers to methods employed to fabricate structures on surfaces with micron and submicron feature sizes. Commonly, the structures made are integrated electronic circuits, although the methods may also be applied to fabricating the elements of integrated biosensors, biochips, microreactors, microanalyzers, and other similar biologically relevant devices. Methods employed include, for example, precision spin-coating of polymeric layers, photoresist masking, reactive ion etching, solution-phase etching, and vapor-phase and solution-phase deposition of materials.

"Photoresist" refers to a material that, upon irradiation, sustains a chemical reaction that allows irradiated and non-irradiated regions to be separated from one another. Although the separation may be simultaneous with the irradiation step (e.g., in laser ablation), it often requires an additional process step or steps (e.g., exposure to a developer). The chemical reaction may involve the formation or breakage of chemical bonds with such bond changes occurring in either an intramolecular or intermolecular fashion. In most applications, a photoresist is applied to a flat surface as a relatively thin liquid layer and evaporated. A "negative photoresist" refers to a photoresist that leaves photoresist on the surface in irradiated regions, while a "positive photoresist" refers to a photoresist that leaves photoresist on the surface in regions that were not irradiated. Certain positive photoresists comprise a base soluble component with phenolic hydroxyl groups. Within such photoresists, "base soluble" refers to a component with groups having a $pK_a$ of about 10 that are solubilized by aqueous solutions having a pH greater than about 10, and more preferably greater than about 11.

A "polymer" is a molecule in which individual molecular units are repetitively linked by covalent bonds. A photoresist polymer provided herein generally comprises multiple molecular units covalently linked to one another through amide bonds.

"Radiation" refers to energy that may be selectively applied, including energy having a wavelength of between $10^{-14}$ and $10^4$ meters. Radiation includes electrons, x-rays and particles from radioisotopic decay, as well as light (e.g., visible, ultraviolet or infrared).

"Solvent Resistance" refers to the ability of a polymeric film to maintain integrity and impermeability while in contact with a particular solvent. A film is "solvent resistant" if contact with a particular solvent does not result in detectable cracking or dehiscence, or significant film dissolution, in the region where it is desired to place an array of compounds. Detectable cracks or dehiscence means cracks or dehiscence detected visually, or by light or phase-contrast microscopy. Significant film dissolution is defined as greater than 50% loss of film thickness after contacting the film with a particular solvent for a particular time period, and may be tested using profilometry or interferometry. It will be apparent that dehiscence, cracks, or loss of more than 50% of film thickness may be tolerated over regions where it is not desired to place an array of compounds. In some embodiments, the solvent resistance of a particular polymeric composition will be a function of film thickness. For instance, films that exceed a particular critical thickness will often crack in a particular solvent, presumably from solvent-induced stresses in the film that exceed the adhesive forces between the film and the substrate.

"Stripping" refers to the substantial removal of photoresist by strippers. Strippers are liquid chemical media used to remove photoresists.

"Substantially homogeneous" refers to miscibility of more than one type of polymer in the solid-phase. For example, a photoactive polyamide derivative and photoinactive polyamide form a substantially homogeneous blend when they are miscible with one another in the solid-state as evidenced by no detectable phase-separation.

Photosensitive Compound and Compositions

Photoresist compositions provided herein comprise one or more photoactive polyamide derivatives. Within such derivatives, at least a portion (e.g., at least 5%) of polymeric repeats bear the following photolabile N-alkyl-o-nitroanilide linkage:

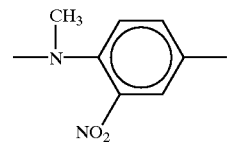

Irradiation of the N-alkyl-o-nitroanilide group results in intramolecular photo-oxidation as follows:

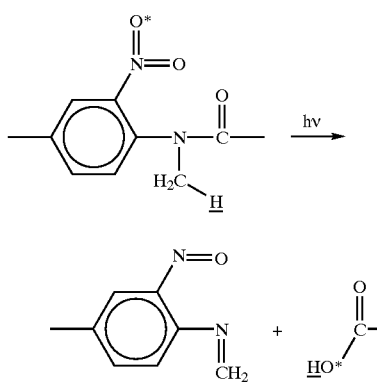

The indicated hydrogen and oxygen atoms of the carboxyl group are derived from the methyl and nitro groups, respectively. This reaction is known to be substantially inert with respect to intermolecular side-reactions with other molecules [see review by Pillai, Synthesis 1980 (1980) p. 1]. As such, it is compatible with methods in which the photoresist compositions provided herein are used to mask reagents to a surface bearing attached molecules, so as to perform regionally selective solid-phase synthesis.

Without wishing to be limited by any particular theory, it is hypothesized that the photopatterning mechanism is a consequence of both polymer chain cleavage and the appearance of acidic carboxyl groups. The proposed model suggests that chain cleavage provides solvent entry points and leads to decreased interdigitation of polymers. These factors together facilitate the preferential solvation and etching of irradiated regions. It is likely that such entry points are further widened by deprotination of the carboxyl group at the site of chain cleavage by basic developer components. The cyclic process of entry point widening and short chain solvation leads eventually to complete dissolution of irradiated regions. This model would predict that a basic developer component is necessary but not sufficient for developer function. Consistent with this model, developer compositions comprising only aqueous base or organic base generally fail to etch irradiated regions. Similarly, developer compositions comprising only non-base components fail to etch irradiated regions of the photoresist, or etch them incompletely.

Within certain embodiments, a photosensitive composition comprises (e.g., at least 25 weight percent) a polyamide derivative that has a repeating unit represented by the following general formula:

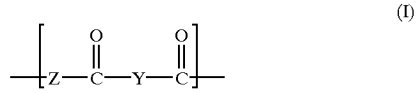

(I)

wherein Z comprises from 20 to about 50 mole percent, and more preferably 20 to about 35 mole percent of:

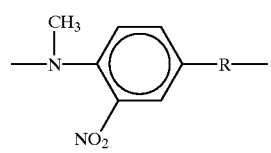

with the balance comprising

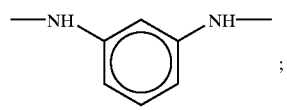

wherein Y comprises from 10 to about 100 mole percent of isophthaloyl radical:

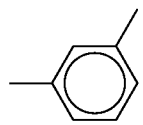

with the balance comprising terephthaloyl radical:

and wherein R is a divalent organic group. In some embodiments R may be selected from the group consisting of:

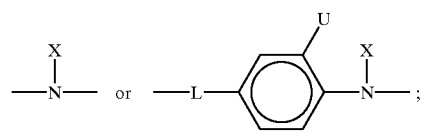

wherein X is H or $CH_3$; L is direct link, O, $CH_2$, $N(CH_3)$, $C(CH_3)_2$, $C(CF_3)_2$, $S_2$, CO, CONH, $O(C_6H_4)_2$, S, $C(C_6H_5)_2$, or $C(CF_3)(C_6H_5)$; and U is H, $NO_2$, or $CH_3$. In preferred embodiments R is NH.

The polyamides represented by formula (1) may be prepared by the solution condensation of one or more diacid chlorides (providing the Y component) and one or more diamines (providing the Z component). Suitable diacid chlorides include isophthaloyl chloride, terephthaloyl chloride, and mixtures thereof. Suitable diamines may be, for example, a mixture of 1,3-phenylene diamine and an N-alkyl-2-nitro diamine such as:

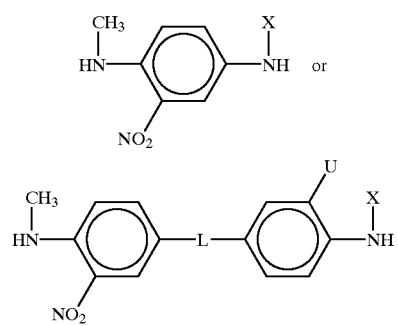

where X is H or $CH_3$; L is direct link, O, $CH_2$, $N(CH_3)$, $C(CH_3)_2$, $C(CF_3)_2$, $SO_2$, CO, CONH, $O(C_6H_4)_2$, S, $C(C_6H_5)_2$, or $C(CF_3)(C_6H_5)$; and U is H, $NO_2$, or $CH_3$. In preferred embodiments the N-alkyl-2-nitro diamine is $N^1$-methyl-2-nitro-p-phenylenediamine, or 3,3'-dinitro-4,4'-di-N-methylaminodiphenyl ether. A preferred photoactive polyamide derivative is formed by the condensation of a diamine mixture of 20 to 50 mole percent of Ni-methyl-2-nitro-p-phenylenediamine, with the balance 1,3-phenylenediamine, with a diacid chloride mixture. Another preferred photoactive polyamide derivative is formed by the condensation of a diamine mixture of 50–100 mole percent of an N-alkyl-2-nitro diamine, with the balance (if any) 1,3-phenylenediamine, with a diacid chloride mixture. One preferred diacid chloride mixture comprises 10–100 mole percent isophthaloyl chloride, with the balance (if any) terephthaloyl chloride.

The mole ratio (i.e. "r") of diamines to diacid chlorides is generally in the range 0.909–1.100. Ratios in the range 0.980–1.020 are preferred. It has been found that the solvent-resistance of the photopolymer is strongly dependent on a portion of high-molecular-weight polymers. According to basic polymer theory, the number average degree of polymerization ($\overline{X}_n$) at 100 percent reaction completion is given by:

$$\overline{X}_n = \frac{(1+r)}{(1-r)}$$

where r is the mole ratio of the two monomers in a particular A-B Type polymerization reaction. For the above ratios, $\overline{X}_n$ will have a value greater than 15, preferably greater than 20, more preferably greater than 50, and still more preferably greater than 100. Values less than about 15 generally result in solvent sensitive compositions.

The solution condensation may be performed by charging the diacid chlorides into a sealable reactor fitted with a heavy stirrer and nitrogen purge, and containing a suitable volume of a solvent (e.g., N-methylpyrrolidone, also referred to herein as NMP) and excess pyridine. Other suitable solvents include dimethylacetamide, hexamethylphosphoric triamide and tetramethylurea. The volume of solvent will preferably result in at least a 5 weight percent final polymer solution. To this is added solid N-alkyl-2-nitro diamine. The solution is allowed to react for sufficient time to condense substantially all the added N-alkyl-2-nitro diamine (i.e., greater than 80%). Typically this requires from 2 to 12 hours. Afterwards, the 1,3-phenylene diamine is added and the reaction is allowed to progress a further 24 hours to complete the polymerization. When the stoichiometry of the reactants is imbalanced, it is preferred to add a quenching or chain terminating compound after polyamide formation. The quenching or chain terminating compound is typically an aromatic compound reactive to the excess monomer. For example, stoichiometries with excess diamine will be terminated with benzoyl chloride, and stoichiometries with excess diacid chloride will be terminated with aniline. The polymer is then precipitated, washed, dried under vacuum, and resuspended in a suitable solvent. Preferably the polymer is resuspended in NMP.

It has been discovered, within the context of the present invention, that the above two-stage addition of diamine is necessary in order to obtain high-molecular-weight polymers with an even distribution of the N-alkyl-2-nitro diamine. The N-alkyl groups of the alkyl-2-nitro diamine are significantly less reactive than the amino groups of 1,3-phenylene diamine. As such, simultaneous addition of both diamines to the diacid chlorides yields polymers that substantially only incorporate 1,3-phenylene diamine. The formed polymers are incapable of further reaction with the N-alkyl groups leaving the majority of the N-alkyl-2-nitro diamine unincorporated (solution remains deep red). By adding the N-alkyl-2-nitro diamine first, the condensation reaction is favored by an excess of diacid chlorides. The reaction yields trimers terminated with -COCl groups that have a reactivity indistinguishable from the remaining unreacted diacid chlorides (solution turns pale-yellow). In the second-stage, the addition of 1,3 phenylene diamine completes the polymerization with the formation of random copolymers of 1,3 phenylene diamine with trimers and diacid chlorides. With the two-stage addition there is a marked increase in viscosity.

It has been further discovered, within the context of the present invention, that the low reactivity of the N-alkyl-2-nitro diamine limits the ability to form high-molecular weight polymers even with a two-stage process when it comprises the majority of Z. For example, in a composition of (1) where the N-alkyl-2-nitro diamine comprises 100% of Z, it is found that the polymerization reaction substantially ceases before forming high-molecular weight polymers (change in coloration is incomplete and viscosity never increases). Such compositions have poor solvent resistance. Although the condensation between N-alkyl groups and -COCl groups proceeds efficiently in the context of excess acid chloride, it is hypothesized that the condensation rate between N-alkyl groups and -COCl groups on extended polymers is so kinetically inefficient that the polymerization effectively terminates. As discussed below, this limitation may be overcome by polymerizing the more reactive unalkylated 2-nitro-diamine to form a high-molecular weight polymer, followed by alkylating the amide nitrogens of the polymer.

Within further embodiments, a photosensitive composition comprises (e.g., at least 25 weight percent) a polyamide derivative that has a repeating unit represented by the following general formula:

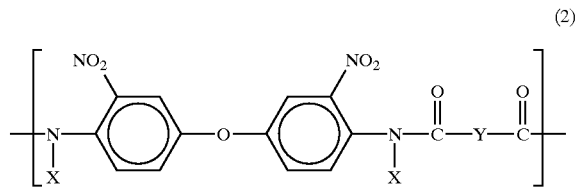

(2)

wherein X comprises from 10 to 100 mole percent $CH_3$ with the balance comprising H; and Y comprises from 0 to 50 mole percent of:

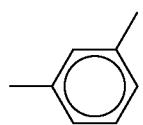

with the balance comprising

Within further embodiments, a photosensitive composition comprises (e.g., at least 25 weight percent) a polyamide derivative having a repeating unit represented by the following general formula:

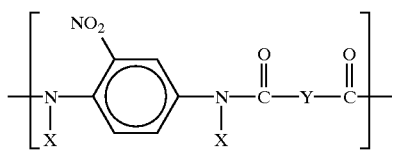

wherein X comprises from 10 to 50 mole percent $CH_3$, and more preferably 10 to 20 mole percent $CH_3$, with the balance comprising H; and Y comprises from 20 to 100 mole percent of:

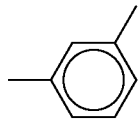

with the balance comprising

Polyamides represented by formulas (2) and (3) are preferably prepared by the solution condensation of diacid chlorides (providing the Y component) and a 2-nitro-diamine. Suitable diacid chlorides include isophthaloyl chloride, terephthaloyl chloride, and mixtures thereof (e.g., 0–50 mole percent isophthaloyl chloride, with the balance terephthaloyl chloride). The diamine may be either 2-nitro-p-phenylenediamine, or 3,3'-dinitro-4,4'-diaminodiphenyl ether. The mole ratio of diacid chloride(s) to the 2-nitro-diamine is as discussed above for the polyamide represented by formula (1).

The solution condensation may be performed by charging the diacid chlorides into a sealable reactor fitted with a heavy stirrer and nitrogen purge, and containing a suitable volume of a solvent such as NMP and excess pyridine. Other suitable solvents include dimethylacetamide, hexamethylphosphoric triamide, and tetramethylurea. The volume of solvent will preferably result in at least a 5 weight percent final polymer solution. To this is added solid 2-nitro-diamine. The solution is allowed to react for 24 hours. A quenching or chain terminating compound is added after polyamide formation. Preferred terminating compounds are monovalent organic groups, such as:

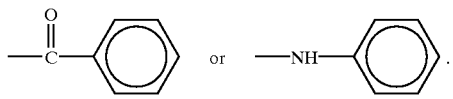

The resulting photoinactive polyamide is then precipitated, washed, and dried under vacuum.

Polymer alkylation with methyl radicals, to yield photoactive polyamide, may be performed by solubilizing the polymer in a quantity of NMP. In some embodiments the polymer is initially insoluble in NMP and a slurry is formed instead of a homogeneous solution. A slurry of sodium hydride is then added dropwise to the solvent mixture under either nitrogen or argon. Addition of sodium hydride solubilizes initially insoluble polymers, and causes an intense brown-orange coloration indicating deprotonation of the amide nitrogen. The mixture is stirred for several minutes or until the production of $H_2$ gas slows. Iodomethane is then added and the mixture is stirred for several hours. The polymer is then precipitated, washed, dried under vacuum, and resuspended in a suitable solvent. Preferably the polymer is resuspended in NMN to a concentration of greater than 30 weight percent. The percentage of amide nitrogens alkylated may be varied by varying the mole ratio of sodium hydride to polymer amide nitrogens. In general, increasing the percentage of amide nitrogens alkylated results in decreasing solvent-resistance. Preferably, alkylation occurs at 10–100 mole percent of amide nitrogens (as determined, for example, by elemental analysis or NMR).

In preferred embodiments of the above photoactive polyamides, polymer ends are capped with phenyl groups, and the number average degree of polymerization ($\overline{X}_n$) is greater than 15, preferably greater than 20, more preferably greater than 50, and still more preferably greater than 100. In general, increasing X, Y, or Z beyond the range specified for each of the above embodiments results in decreasing solvent resistance of the dried films.

Photoresist solutions are generally prepared by dissolving one or more of the above photopolymers in one or more solvents. Because of the intended solubility profile of the disclosed polyamide derivatives, the selection of suitable solvents is limited. Preferred solvents are N-methylpyrrolidone (NMP) and dimethylacetamide (DMAC). In preferred embodiments, additional solvents may be added to NMP and DMAC in such proportions as to give desirable evaporation characteristics without precipitating the polymer. For example, propylene glycol monomethyl ether acetate (PGMEA) may be used up to 20 volume percent. The total amount of solvent used to prepare the liquid photoresist may range from 50 to 99 weight percent of the solution, limited only by the solubility of the photopolymer.

Additives such as colorants, dyes, surfactants and plasticizers may be added to the photoresist solution before it is applied to a substrate. Examples of dye additives that may be used together with the photoresist compositions of the present invention include Methyl Violet 2B (C.I. No. 42000), Victoria Blue B (C.I. No. 44045) and Neutral Red (C.I. No. 50040) at one to five weight percent based on the weight of polyamide. The dye additives help provide increased resolution by inhibiting back scattering of light off the substrate. Surfactants promote the planarization of an applied liquid film of photoresist A preferred surfactant is Triton X-100™ at one to three weight percent based on the weight of polyamide. In some embodiments, photoimageable blends are formed between the photopolymer and up to 75 weight percent of a photoinactive polyamide. Although such blends have a lower photosensitivity, the photoinactive component may increase the solvent resistance and strength of the base photopolymer. Such blends are preferably substantially homogeneous (i.e., there is no detectable phase-separation).

Methods Employing Photoresist Compositions

A photoresist composition may be applied to a substrate by any conventional method used in the photoresist art, including dip-coating, spraying, whirling, spin-coating and microdispensing. When spin coating, for example, the photoresist solution can be adjusted as to the percentage of solids content in order to provide a coating of the desired thickness given the type of spinning equipment utilized and the amount of time allowed for the spinning process. Suitable substrates include, for example, silicon, aluminum or polymeric resins, silicon dioxide, doped silicon dioxide, silicon nitride, tantalum, copper, polysilicon, ceramics and glass. A substrate may also comprise various polymeric resins especially transparent polymers such as polyesters. All operations in the process of applying, irradiating and developing a photoresist should be carried out in a room lit primarily or entirely by light of a wavelength outside of the light range which will react with the photoresist. This may be accomplished with a protective golden shield or sleeve that blocks light less than 505 nm, placed over standard cool-white fluorescent lights (Imtec Products Inc., Sunnyvale, Calif.).

After the photoresist solution is coated onto the substrate, a photoresist layer may be generated by evaporating the solvent. For example, the substrate may be baked (e.g., at about 85° C. to 90° C. for a few minutes) until substantially all the solvent has evaporated and only a thin, continuous coating of photoresist remains on the substrate. In preferred embodiments, the coating is 0.2 $\mu$m to 4.0 $\mu$m thick. Following this soft-bake, the substrate is further baked for several minutes at 110° C. to 135° C. It has been discovered that this hard-bake is necessary to completely remove solvent and create a coating with the desired solvent resistance. Incomplete solvent removal leads to a coating that loses integrity upon contact with various solvents.

The coated substrate is then selectively exposed to actinic radiation in any desired exposure pattern. The photolabile component of the photopolymer has a $\lambda_{max}$ of 365 nm while the photoinactive component has a $\lambda_{max}$ of 320 nm. Maximum cleavage of photolabile linkages is thus achieved with I-line (365 nm) radiation. Such radiation is not absorbed by the bonds typically found in molecules, obviating the possibility of directly photodegrading surface-attached molecules during photoresist-directed solid-phase synthesis. Such irradiation permits the selective, substantial removal of photoresist from irradiated regions. This property results from differential solubility of irradiated photoresist, as compared to non-irradiated photoresist. The extent of this differential solubility may be assessed by exposing a selectively irradiated photoresist layer to developer and assessing the extent to which photoresist has been removed from irradiated and non-irradiated regions (e.g., using profilometry). In general, irradiation that results in a differential solubility of at least 20-fold is sufficient.

Selective irradiation may be achieved using suitable masks, negatives, stencils, templates, etc. For example, one or more masks and photolithographic techniques of the type known in the semiconductor industry (see Sze, VLSI Technology, McGraw-Hill (1983), and Mead et al., Introduction to VLSI Systems, Addison-Wesley (1980)) may be used. Light is preferably directed at the surface layered with the photoresist, but may also be directed at the back of the substrate, so long as it is transparent to the wavelength of light needed to react with the photoresist. The photoresist may be irradiated either in contact or not in contact with a solution, and is preferably irradiated not in contact with a solution. Using the photolithographic methods disclosed herein, it is possible to mask light to very small and precisely known locations, thereby achieving a method with exemplary reproducibility and dimensional control consistent with, for example, the production of substrates bearing ligand-arrays with micron-scale features.

A mask employed for the selective irradiation is generally an opaque support with transparent regions that allow the free passage of light to selected regions of the photoresist. Opaque regions may block light by absorbing or reflecting it. Within preferred embodiments, an ordered sequence of masks is used. In some embodiments it is possible to minimize the number of masks by utilizing the same mask to irradiate different regions by translating and/or rotating the mask with respect to each of the regions. A mask may be, for example, a glass sheet having etched chrome thereon or a silver-halide film with opaque regions obtained by laser-photoplotting. Such masks are manufactured by, for example, Precision Image Corporation, Redmond, Wash.

The transparent regions of a mask are in a pattern substantially identical to the pattern of light that will irradiate the photoresist layer, and permit the passage of light in a pattern that corresponds to the irradiated regions. The transparent regions may be of any size or shape. For example, squares, ellipsoids, rectangles, triangles, circles, or portions thereof, along with irregular geometric shapes, may be utilized. In preferred embodiments, the area of each transparent region is extremely small being between about 1 $cm^2$ and $10^{-12}$ $cm^2$, preferably less than 0.3 $cm^2$, and most preferably between about 1 $\mu m^2$ and 1 $mm^2$. For example, a transparent region may have an area less than about $10^{-1}$ $cm^2$, $10^{-2}$ $cm^2$, $10^{-3}$ $cm^2$, $10^{-4}$ $cm^2$, $10^{-5}$ $cm^2$, $10^{-6}$ $cm^2$, $10^{-7}$ $cm^2$ or $10^{-8}$ $cm^2$. In preferred embodiments, a mask comprises a plurality of transparent regions. In some embodiments, a mask comprises more than $10^2$, $10^3$, $10^4$, $10^5$, $10^6$, $10^8$ or $10^9$ separate transparent regions. In preferred embodiments, a mask comprises greater than 100 duplicates of an array of separate square or circular transparent regions, each array comprising greater than $10^3$, $10^4$, $10^5$ or $10^6$ transparent regions. It will be understood, of course, that the irradiated regions of a photoresist layer will have sizes, shapes and numbers substantially identical to the transparent regions of the mask.

During irradiation, a mask is brought into close proximity with, imaged on, or preferably brought directly into contact with the photoresist surface. In alternative embodiments, the mask may be some distance away from the photoresist surface, as occurs in the technique known as projection printing. Alignment may be performed using conventional alignment techniques in which alignment marks are used to accurately overlay successive masks, or more sophisticated techniques may be used. For example, interferometric techniques may be used (see Flanders, *App. Phys. Lett.* 31:426, 1977).

With the mask appropriately positioned over the photoresist, the mask is irradiated with light. The light may be from a conventional incandescent source, a UV source, a laser, a laser diode, an excimer laser, an x-ray source, a programmable mask, a fiber optic or the like. For example, a photoresist layer may be irradiated with 365 nm light from a UV transilluminator manufactured by UVP Inc. (Upland, Calif.) at an energy density of 8 $mW/cm^2$ for sufficient time to permit substantial removal of irradiated photoresist by developer (e.g., for 1–2 minutes).

To enhance the contrast of light applied to the photoresist, contrast enhancement materials may be provided between the mask and the photoresist. A contrast enhancement layer may comprise a molecule that is decomposed by light or transiently bleached by light. Transient bleaching of materials allows greater penetration where light is applied, thereby enhancing contrast. Poor contrast due to standing waves and reflective notching may be reduced by applying an anti-reflective coating, for example, ARC® coating manufactured by Brewer Science Inc., Rolla, Mo. Alternatively, contrast enhancement may be provided by way of a cladded fiber optic bundle. The use of contrast enhancement materials is well known in the art.

As alternatives to the use of masks, other methods may be used to illuminate selected regions of photoresist. For example, the substrate may be translated under a modulated laser or diode light source (see Feyrer et al., U.S. Pat. No. 4,719,615). In alternative embodiments, a laser galvanometric scanner may be utilized. In other embodiments, the irradiation of the photoresist may take place on or in contact with a fiber optic light source, or a liquid crystal. By appropriately modulating liquid crystals, light may be selectively controlled so as to permit light to contact selected regions of the photoresist. Such a liquid crystal is also referred to as a "programmable mask," or an integrated circuit spatial light modulator (ICSLM), manufactured by Displaytech (Boulder, Colo.). Another programmable mask comprises millions of micron-scale mirrors individually controllable on an integrated silicon chip surface as manufactured by Texas Instruments. Alternatively, irradiation may take place on the end of a series of optical fibers to which light is selectively applied. In some embodiments, light will be directed to extremely small regions, being limited by diffraction to a size directly proportional to the wavelength of light. In order to mask illumination to regions smaller than a wavelength of light, more elaborate techniques may be utilized. For example, light may be directed at the photoresist by way of molecular microcrystals on the tip of, for example, micropipettes (see Lieberman et al., Science 247:59, 1990). Other means of controlling the location of light exposure will be apparent to those of skill in the art.

After the irradiating step is completed, the photoresist is contacted with developer. This results in the selective, substantial removal of photoresist from irradiated regions, leaving photoresist only in discrete regions. The developer is non-aqueous and preferably contains a basic compound (i.e., a compound that would, if dissolved in water, have a $pK_a$ greater than 7, and more preferably greater than 9). The developer may also contain various surfactants. Contact with developer may be by any suitable method, including immersion, although other methods of applying the developer exist including, for example, spraying, puddling and streaming. The rate of photoresist dissolution can be increased by increasing the concentration of the basic compound, and by increasing the temperature, limited mainly by solubility considerations of remaining unirradiated photoresist. In a preferred embodiment, irradiated photoresist is contacted with developer at a temperature from 20° C. to 30° C., and most preferably at a temperature from 23° C. to 27° C., for sufficient time to effect substantial removal of desired regions of the irradiated photoresist. Typically, photoresist is substantially removed after about 5 to 10 minutes of immersion.

Suitable developers comprise non aqueous mixtures of solvents containing ketone, amino, hydroxyl, and amide moieties. Representative mixtures which may be used to develop each of the embodiments represented by formulas (1), (2) and (3) are shown in Table 1.

TABLE I

Representative Developer Solutions

| Photopolymer Formula | Developer Solutions (volume %) |
|---|---|
| 1 | a. 15% ethanolamine, 85% cyclohexanone |
|   | b. 15% ethanolamine, 85% acetone |
| 2 | a. 40% NMP, 60% ethanol |
|   | b. 50% ethanolamine, 50% formamide |
|   | c. 11% ethanolamine, 89% methanol |
| 3 | a. 10% triethanolamine, 90% acetone |
|   | b. 25% DMF, 25% ethanolamine, 50% acetone |

DMF is dimethylformamide

It will be understood that these are representative developers, and they should not be construed as providing conditions, parameters, or values that must be utilized exclusively in order to practice the present invention. It will also be understood that the values of X, Y and Z will determine, in part, the optimal developer for a given photopolymer composition.

After removal of the substrate from the developing solution, the patterned film of photoresist is generally rinsed with a suitable volatile solvent so as to remove residual developer. In preferred embodiments the rinse solvent is acetonitrile. A post-rinse heat treatment or bake may be employed to further increase the solvent-resistance of the film. For example, the film may be heated at a temperature from about 90° C. to 135° C. for about one minute. The photoresists provided herein demonstrate excellent thermal stability. Although extremes of temperature are generally avoided in preferred applications, films have been heated to over 300° C. with no evidence of degradation.

A patterned film prepared as described herein is resistant to numerous solvents, such as the solvents and solvent mixtures shown in Table II. In general, the films are readily soluble in N-alkyl amide solvents including DMF, NMP, and DMAC. The films are also readily solubilized by a mixture of 85% cyclohexanone, 10% ethylene glycol monoethyl ether, and 5% water.

TABLE II

Representative Solvents in which Photoresists are not Soluble

| | | |
|---|---|---|
| acetonitrile | 85% CYC + 15% triethylamine | 50% butyraldehyde + 50% ethylene glycol |
| acetone | CYC + ammonium hydroxide | 50% TEA + 50% acetone |
| ethanol | CYC + sodium dodecyl sulfate | 33% TEA + 33% acetone + 33% water |
| methanol | CYC + calcium chloride | 30% ethanolamine + 70% formamide |
| formamide | 85% CYC + 15% ethanol | 10% DMF + acetone |
| PGMEA | 85% CYC + 15% methanol | 25% triethyl amine + 75% acetone |
| cyclohexanone | 77.5% CYC + 15% ET + 7.5% DMAC | 10% TA + 10% AA + 20% water + 60% ET |
| toluene | 85% CYC + 15% ethylene glycol | 13% TA + 37% formamide + 50% ethanol |
| ethylene glycol | 90%.CYC + 10% pyridine | 20% TA + 20% EA + 60% acetone |
| tetrahydrofuran | 90% CYC + 10% EGMEE | 10% ethanol amine + 90% ethanol |
| dichloromethane | 85% CYC + 10% EGMEE + 5% TA | 80% formamide + 20% water |
| ethanolamine | 85% CYC + 10% EGMEE + 5% wafer | 50% ethanol + 50% formamide |
| triethanolamine | 85% CYC + 15% morpholine | 10% NMP + 90% ethanol |
| EGMEE | 85% CYC + 15% ethanolamine | 11% ethanolamine + 89% methanol |

TABLE II-continued

Representative Solvents in which Photoresists are not Soluble

| piperidine | cyc + acetic acid | 1% ethanolamine + 99% acetonitrile |

PGMEA = propylene glycol monomethyl ether acetate; EGMEE = ethylene glycol monoethyl ether; EA = ethanolamine; AA = t-amyl alcohol; TA = triethylamine; ET = ethanol; TEA = triethanolamine; CYC = cyclohexanone.

It will be apparent that a photoresist layer generated as described above may be used for a variety of applications. For example, such photoresists may be used in the preparation of ligand arrays. Briefly, regions of a support from which photoresist has been removed are contacted with at least one reagent. This may be achieved by contacting the entire photoresist layer with the reagent, since the reagent reacts only with molecules in exposed region(s). Liquid reagents may be applied to the support surface using several techniques including, but not limited to spraying, dipping, microdispensing or combinations thereof. Although reagents are preferably applied to the surface using solution-phase methods, it will be apparent to those skilled in the art that vapor-phase methods are also possible.

The types of reagents that may be used to synthesize array components are without restriction. In preferred embodiments, the reagents are elements of solid-phase synthesis methods that yield biopolymers or pharmacologic analogues. Reagents are preferably precursors of organic polymers such as polynucleotides, polypeptides, peptide nucleic acids, morpholino-based nucleobase polymers, peptide-based nucleic acid mimics (PENAMs) and nuclease resistant polynucleosides.

Biopolymer ligands may be synthetically established on the surface by solid-phase nucleic acid synthesis (e.g., phosphoramidite or H-phosphonate methods), solid-phase peptide synthesis (eg., the "Merrifield Method", see Merrifield, *J. Am. Chem. Soc.* 85:2149, 1963) or solid-phase peptide nucleic acid synthesis (see Egbolm et al., *J. Am. Chef Soc.* 114:1895, 1992). Agents with known or potential pharmacologic activity available by solid-phase synthesis include, for example, analogues of beazodiazepine, sulfonamide, hydantoiu, miconazole, dihydropyridone, pyazolone, pyrimdine, quinazoline, quinazolinone, oligocarbamates, peptoids, peptidyl phosphonates, and carboxyalkyldipeptides (see Gordon et al., *J. Medicinal Chem.* 37:1385, 1994 and *The Combinatorial Chemisty Catalog*, Nova Biochem, Inc., 1998). Other small-molecule syntheses are possible using organic reactions known to occur on the solid-phase. The preparation of such arrays is described in copending application entitled, "Method and Composition For Performing an Array of Chemical Reactions on a Support Surface" (U.S. application Ser. No. 09/326,479).

Following reaction with the reagent(s), a photoresist layer may be stripped. The stripping process should substantially remove the entire photoresist layer. In other words, as noted above, the photoresist should be sufficiently removed to permit a desired reaction between underlying molecules and a reagent. Such a reaction should proceed at a yield that is at least 50%, and more preferably at least 90% of the yield observed for similar molecules that have not previously been coated with photoresist. Reaction yields may be readily determined with and without photoresist using standard techniques appropriate for the reaction of interest. As noted above, preferred stripping solutions comprise N-alkyl amide solvents such as DMF, NWP or DMAC. Another preferred stripping solution is a mixture of 85% cyclohexanone, 10% ethylene glycol monoethyl ether and 5% water.

The above process (coating with photoresist, selective irradiation of photoresist, substantial removal of photoresist from irradiated regions, reaction of exposed molecules within irradiated regions and removal of the remaining photoresist) may be repeated as many times as desired to achieve synthesis of different molecules in discrete known regions. It will be apparent that, within each subsequent step, irradiation may be targeted to regions that are the same as in previous steps, to regions in separate locations, or to regions that overlap previous regions to varying degrees.

It will be apparent that the compositions provided herein have numerous advantages over previous photoresist compositions, including the important advantage of providing a photosensitive film that maintains integrity and impermeability in a variety of solvents. Compositions provided herein further have applications outside the field of solid phase organic synthesis. For example, photoresists as described herein may be used as a barrier layer to reagents in the vapor-phase as well as the liquid-phase. The invention may also find use as a patterned insulating layer in microcircuitry applications, as masks in vapor deposition processes, ion implantation processes, etc. Similarly, the photoresists of this invention may be used in the preparation of printing plates, lithographic proofing applications, lithographic transfer foils, and other similar applications.

The following Examples are offered by way of illustration and not by way of limitation. Within the following Examples, all reagents were from the Aldrich Chemical Company, Inc., Milwaukee, Wis. unless indicated to the contrary.

EXAMPLES

Example 1

Preparation of 3,3'-dinitro-4,4'-diacetamidodiphenyl Ether

This Example illustrates the preparation of the representative photoresist compound:

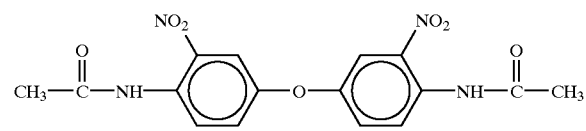

To a 70° C. solution of 25 grams (0.125 mole) of 4,4'-diaminodiphenyl ether in 90 ml of glacial acetic acid was added 28.55 ml (0.286 mole) of acetic anhydride. The acetic anhydride was added dropwise at such a rate and with heating to maintain a temperature between 90° C. and 100° C. After the addition of acetic anhydride, the temperature was maintained between 90° C. and 100° C. for an additional hour. The reaction mixture was further reacted at room temperature overnight forming a precipitate. The mixture was filtered, and the collected precipitate dried at room temperature to give 32.6 grams of 4,4'-diacetamidodiphenyl ether, m.p. 228–230° C. (lit. m.p. 228–229° C.). The yield was 91.8% of the theoretical amount.

To 186 ml of acetic anhydride was added 25.3 ml of 70% nitric acid. The nitric acid was added dropwise at such a rate as to maintain a temperature less than 20° C. This required external cooling of the reaction mixture with an ice-bath. After the addition was complete, the mixture was cooled to between 0° C. and 5° C. While rapidly stirring the mixture, 20 grams (0.070 mole) of 4,4'-diacetamidodiphenyl ether was added rapidly. Within 2 minutes a bright yellow precipitate formed that precluded further stirring. The reaction mixture was left to sit at room temperature for 30 minutes, then poured into 800 ml of a 1:1 mixture of ice and water. The slurry was stirred for 15 minutes and then filtered. The precipitate was collected and added to another 800 ml of a 1:1 mixture of ice and water, and stirred for an additional 15 minutes. The yellow precipitate was collected and dried under vacuum at room temperature to give 25.8 grams of 3,3'-dinitro-4,4'-diacetamidodiphenyl ether, m.p. 213–215° C. (lit. m.p. 211–214° C.). The yield was 97.7% of the theoretical amount.

Example 2

Preparation of 3,3'-dinitro-4,4'-diaminodiphenyl Ether

This Example illustrates the preparation of the representative photoresist compound:

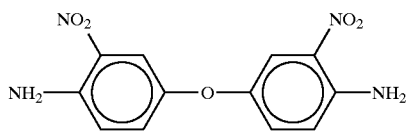

To a slurry of 13.2 grams (0.035 mole) of 3,3'-dinitro-4,4'-diacetamidodiphenyl ether in 106 ml of methanol was added 9.28 grams of potassium hydroxide. The mixture was stirred at room temperature for 3 hours, and then poured into 166 ml of water. The orange precipitate that formed was collected, giving 9.0 grams of crude 3,3'-dinitro-4,4'-diaminodiphenyl ether, m.p. 175–178° C. In order to purify the crude further, the crude was added to 300 ml of 95% ethanol and heated to between 72° C. and 74° C. at which point all of the crude was solubilized. The mixture was then cooled over several hours to give 6.6 grams of deep red crystals that were 3,3'-dinitro-4,4'-diaminodiphenyl ether, m.p. 180–181° C. (lit. m.p. 179–180° C.); $^1$H NMR (in CDCl$_3$ using TMS as the internal standard) δ 6 5.99 (s, 2H, NH$_2$), δ 6.85 (d, 1H, Ar), δ 7.17 (q, 1H, Ar), δ 7.69 (d, 1H, Ar). The yield was 65% of the theoretical amount.

Example 3

Preparation of 3,3'-dinitro-4,4'-di-N-methylaminodiphenyl Ether

This Example illustrates the preparation of the representative photoresist compound:

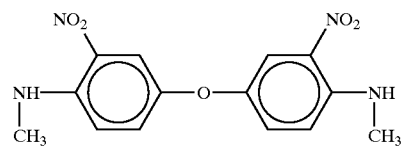

To a slurry of 20 grams (0.055 mole) of 3,3'-dinitro-4,4'-diacetamidodiphenyl ether in 150 ml of DMF under nitrogen, was added 3.0 grams (0.125 mole) of sodium hydride at such a rate as to maintain a temperature of less than 40° C. An immediate coloration was noted which indicated the formation of a deprotonated amide species. The mixture was left to stir for several minutes or until the rate of H$_2$ gas production slowed. To this mixture, 7.41 ml (0.119 mole) of iodomethane was added dropwise, and the reaction allowed to proceed at room temperature. After 24 hours, NaI crystals formed and were collected by filtration. To the filtrate was added 1–2 liters of NaCl-saturated water with stirring. After several minutes, a dark orange-brown tar formed on the surface of the mixture and was collected with a spatula. The collected material was dried under vacuum to give 15.9 grams of crude 3,3'-dinitro-4,4'-di-N-methylacetamidodiphenyl ether, m.p. 60–62° C. The yield was 74% of the theoretical amount.

To 1.76 grams of the crude 3,3'-dinitro-4,4'-di-N-methylacetamidodiphenyl ether in 13.6 ml of methanol was added 1.20 grams of potassium hydroxide. The mixture was stirred at room temperature for 3 hours, and then poured into 21 ml of water. The red precipitate that formed was collected, giving 1.06 grams of crude 3,3'-dinitro-4,4'-di-N-methylaminodiphenyl ether, m.p. 140–145° C. The yield was 76% of the theoretical amount. The crude was recrystallized twice from 95% ethanol yielding a compound with a distinct m.p. of 196–197° C.; $^1$H NMR (CDCl$_3$/TMS) δ 3.06 (s, 3H, CH$_3$), δ 6.87 (d, 1H, Ar), δ 7.26 (q, 1H, Ar), δ 7.75 (d, 1H, Ar), δ 7.98 (s, 1H, NH).

Example 4

Preparation of N$^1$-methyl-2-nitro-p-phenylenediamine

This Example illustrates the preparation of the representative photoresist compound:

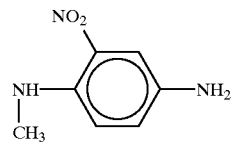

To 39 grams (0.25 mole) of 4-fluoro-3-nitroaniline was added 220 ml (2.83 mole) of a 40 weight percent (12.88 M) aqueous solution of methylamine. The mixture was refluxed for 1.5 hours, during which time the reaction temperature went from 48° C. to 95° C. with an 80 ml loss of volume. An additional 100 ml of 40 weight percent aqueous methylamine was added, and the mixture was refluxed for an additional 2.5 hours. After refluxing, the reaction was cooled to 4° C. for 24 hours. The dark bronze crystals that formed were collected by filtration and dried under vacuum, giving 41.8 grams of N$^1$-methyl-2-nitro-p-phenylenediamine, m.p. 117–118° C. (lit. m.p. 115–116° C.). The yield was quantitative.

Example 5

Preparation of Representative Patterned Photoresist

This Example illustrates the preparation of a patterned photoresist film having desired solvent resistance.

A photoactive polyamide having a repeating unit represented by formula (1) was synthesized by the solution step-polymerization method where Z was formed from a mixture comprising 80 mole percent of 1,3-phenylenediamine and 20 mole percent of N$^1$-methyl-2-nitro-p-phenylenediamine, and Y was formed from an equimolar mixture of isophthaloyl chloride and terephthaloyl chloride. The molar ratio of diamines to diacid chlorides was 1.020 (2% molar excess of diamines). All process steps of the polymerization were performed while working under cool-white fluorescent lights shielded with Gold Shields™ [Imtec Products Inc., Sunnyvale, Calif.].

To 12 ml of NMP was added 1.3533 grams (0.00666 mole) of an equimolar mixture of isophthaloyl chloride and terephthaloyl chloride. The mixture was shaken until the diacid chlorides were completely solubilized. To this mixture was then added 0.2271 grams (0.00136 mole) $N^1$-methyl-2-nitro-p-phenylenediamine and 1 ml of pyridine. The mixture was allowed to react at room temperature for 24 hours, during which time the reaction progress was visually monitored by noting the gradual change of solution color from red to yellow. After this reaction was completed, 0.5882 grams (0.00544 mole) of 1,3-phenylenediamine and 1 ml of pyridine were added. The mixture was allowed to further react at room temperature for 72 hours with a marked increase in viscosity noted. At the completion of polymerization, 0.1 ml (0.00085 mole) of benzoyl chloride was added, and the mixture was allowed to react for an additional 24 hours.

After the polymer chains were suitably terminated, the polyamide was precipitated by adding the entire reaction mixture to 100 ml of acetonitrile. The precipitate was collected by filtration, washed and triturated with acetone, and dried under vacuum to give 0.66 grams of polymer. The yield was 39% of the theoretical amount. The solid polymer was resuspended in 2.2 ml of NMP to afford a concentrated 30 weight percent stock solution.

The stock solution was used to prepare a liquid photoresist that contained 15 weight percent of polymer in a solvent mixture comprising 80% NMP, 20% PGMEA, and 0.2% Triton X100™. The photoresist was centrifuged for 5 minutes at 12,000 r.p.m. to remove any microscopic particulates. The photoresist was then applied to the surface of a glass slide with a pipette, and the excess allowed to drain by vertically positioning the slide on an absorbent towel. The slide was baked at about 85° C. for two minutes, and at about 110° C. for two minutes. The approximately 2 μm thick film was hard, continuous, glassy and firmly adherent to the substrate surface.

The photoresist surface was brought into contact with a mask bearing a 16×16 array of 600 μm×600 μm transparent squares on an opaque background [Precision Image Corporation, Redmond, Wash.]. The transparent squares are separated from one another by 200 μm. The mask was exposed to 365 nm light at an energy density of 8 mW/cm$^2$ for 10 minutes using a UV transilluminator [UVP Inc., Upland, Calif.].

With the photoresist appropriately irradiated, the entire substrate was immersed in developer comprising 15% ethanolamine and 85% cyclohexanone. The photoresist in irradiated regions was completely removed from the substrate surface after about 5 to 10 minutes in developer. After development, the entire substrate was rinsed with acetonitrile, air-dried, and baked at about 110° C. for 30 seconds. A fine resolution positive tone relief image was obtained having well defined line spaces. The sensitivity or photospeed is about 500 mJ/cm$^2$. The solvent-resistance of the film was screened against 30 second immersions in acetonitrile, ethanol, cyclohexanone, and toluene. The film was either classified as solvent-resistant or solvent-sensitive depending on the film's integrity after immersion (see Table III).

Examples 6–28

Preparation of Patterned Photoresists

This Example illustrates the preparation of additional patterned photoresist films.

A series of photoactive polyamides having a repeating unit represented by formula (1) were synthesized by the same method as described in Example 5, except that the ratio and composition of diamines for forming Z, and the ratio of diacid chlorides for forming Y were varied as indicated in Table III. The solvent-resistance of each of the compositions was determined as described in Example 5. Other pertinent features of the polyamides and the polymerization reactions are indicated in Table III. The entry of "C" after the number in the example column indicates a comparative example.

It was generally observed that para radicals increased solvent-resistance, while meta radicals and N-alkylation decreased it. This is consistent with the hypothesis that solvent resistance is the consequence of inter-chain hydrogen bonds formed between amide linkages. Based on this model, it is expected that hydrogen bonding will be disrupted by N-alkylation and randomly bent polymer chains, and will be promoted by extended rod-like chains. Accordingly, it was found that if N-alkyl-2-nitrodiamine comprised greater than about 50 mole percent of Z, the film became solvent-sensitive (compare Examples 5, 12, 14, and 16; and compare Examples 6, 13, and 15).

TABLE III

Solvent Resistance of Representative Photoactive Polyamides

| Example | % Y iso | % Y ter | % Z N-alk | % Z 1,3-phen | % Z 1,4-phen | % Z other diamine | characteristics of photopolymer |
|---|---|---|---|---|---|---|---|
| 5 | 50 | 50 | 20 | 80 | — | — | solvent resistant, imageable |
| 6 | 100 | — | 20 | 80 | — | — | solvent resistant, imageable |
| 7 C | — | 100 | 20 | 80 | — | — | barely soluble in NMP, gels |
| 8 C | 50 | 50 | 20 | — | 80 | — | precipitates in polymerization |
| 9 C | 100 | — | 20 | — | 80 | — | precipitates in polymerization |
| 10 | 10 | 90 | 35 | 65 | — | — | solvent resistant, imageable |
| 11 | 25 | 75 | 35 | 65 | — | — | solvent resistant, imageable |
| 12 | 50 | 50 | 35 | 65 | — | — | solvent resistant, imageable |
| 13 | 100 | — | 35 | 65 | — | — | solvent resistant, imageable |
| 14 | 50 | 50 | 50 | 50 | — | — | partial resistance, imageable |
| 15 | 100 | — | 50 | 50 | — | — | partial resistance, imageable |
| 16 C | 50 | 50 | 100 | — | — | — | solvent sensitive |
| 17 C | 50 | 50 | 35 | — | — | 65[a] | solvent sensitive |
| 18 C | 50 | 50 | 35 | — | — | 65[b] | solvent resistant, not imageable |

TABLE III-continued

Solvent Resistance of Representative Photoactive Polyamides

| Example | % Y iso | % Y ter | % Z N-alk | % Z 1,3-phen | % Z 1,4-phen | % Z other diamine | characteristics of photopolymer |
|---|---|---|---|---|---|---|---|
| 19 C | 50 | 50 | 35 | — | — | 65[c] | solvent resistant, not imageable |
| 20 C | 50 | 50 | — | 100 | — | — | solvent resistant, not imageable | iso = isophthaloyl chloride;
ter = terephthaloyl chloride;
N-alk = N[1]-methyl-2-nitro-p-phenylenediamine;
1,3-phen = 1,3-phenylenediamine;
1,4-phen = 1,4-phenylenediamine;
[a] = 2,5-dimethyl-1,4-phenylenediamine;
[b] = 2,5-dichloro-1,4-phenylenediamine;
[c] = tolidene.

As shown in Examples 8 and 9, when the para content of Z was 100 mole percent, the increase in solvent-resistance was so severe that polymer precipitated during polymerization irrespective of the meta content of Y. The effect was less pronounced when the para content of Y was 100 mole percent as shown in Example 7. In this case, polymer remained in solution during polymerization, but could only be made to form a concentrated stock solution in NMP with great difficulty. The stock solution thus formed was unstable, and gelled after 12 to 24 hours forming what was probably the nematic phase. If Y comprised as little as 10 mole percent of the meta isomer, the corresponding polymer solution was stable (see Example 10). For a given composition of Z, decreasing the meta content of Y generally increased the solvent-resistance, although the effect in some embodiments was qualitative and subtle (as in the series of Examples 13, 12, 11, and 10). Thus, a desirable photosensitive composition is obtained by Y and Z ratios that allow imaging, demonstrate solvent-resistance, but remain soluble in the casting solvent of the photoresist (i.e., NMP).

Attempts to identify solvent-resistant photoresist compositions where Z comprised a mixture of the N-alkyl-2-nitrodiamine, and a substituted diamine were unsuccessful (see Examples 17, 18, and 19). The substituted diamines tested included 2,5-methyl-1,4-phenylenediamine, 2,5-dichloro-1,4-phenylenediamine, and tolidene. These compositions were either solvent sensitive (Example 17), or could not be imaged for unknown reasons (Examples 18 and 19).

Efforts were made to improve solvent-resistance by blending photoactive polymers with a solvent-resistant, but photoinactive polyamide. As shown in Table IV, miscible blends were formed between selected photopolymers from Table III, and up to 85 weight percent of the photoinactive polyamide from Example 20. Although the blends had lower photosensitivity, the photoinactive component was observed to increase the solvent resistance and strength of the base photopolymer. For instance, compare Example 14 with Examples 24–26, and compare Example 16 with Example 27.

TABLE IV

Solvent Resistance of Polymer Blends

| example | % poly. from example 20 | % poly. from example 12 | % poly. from example 14 | % poly. from example 16 | characteristics of polymer blend |
|---|---|---|---|---|---|
| 21 | 25 | 75 | — | — | solvent resistant, imageable |
| 22 | 30 | 70 | — | — | solvent resistant, imageable |
| 23 C | 50 | 50 | — | — | solvent resistant, not imageable |
| 24 | 25 | — | 75 | — | solvent resistant, imageable |
| 25 | 50 | — | 50 | — | solvent resistant, imageable |
| 26 | 75 | — | 25 | — | solvent resistant, imageable |
| 27 | 75 | — | — | 25 | solvent resistant, imageable |
| 28 C | 85 | — | — | 15 | solvent resistant, not imageable | poly. = polymer.

Example 29

Characterization of Comparative Photoresist

This Example illustrates the properties of a comparative photoresist.

A photoactive polyamide having a repeating unit represented by formula (1) was synthesized by the same method as described in Example 5. The composition of Y was formed from 50 mole percent isophthaloyl chloride and 50 mole percent terephthaloyl chloride. The composition of Z was formed from 100 mole percent of 3,3'-dinitro-4,4'-di-N-methylaminodiphenyl ether. The reaction failed to progress as noted by the lack of increased viscosity, and the incomplete change in coloration characteristic of the condensation between an acid chloride and an N-alkyl-2-nitrodiamine (see above). Although the film was photoimageable, it had only partial solvent resistance due presumably to a lack of high-molecular-weight polymer.

Example 30–47

Further Representative Photoresists

The difficulty encountered in Comparative Example 29 may be avoided by first polymerizing a non-alkylated 2-nitro-diamine with the appropriate diacid chlorides to form a high-molecular-weight polymer. The polymerization progresses to a greater degree due to the absence of steric constraints imposed by the N-alkyl groups. The amide nitrogens of the polymer are then alkylated separately. This Example illustrates the use of such a method to prepare photoactive compositions represented by formulas (2) and (3).

According to an Example 30, a non-alkylated polyamide was synthesized by adding 1.3533 grams (0.00666 mole) of terephthaloyl chloride to 20 ml NMP. The mixture was shaken until the diacid chloride was completely solubilized. To this mixture was then added 1.972 grams (0.00680 mole) 3,3'-dinitro-4,4'-diaminodiphenyl ether and 2 ml of pyridine. The mixture was allowed to react at room temperature for 72 hours. A marked increase in viscosity was noted. At the completion of polymerization, 0.1 ml (0.00085 mole) of benzoyl chloride was added, and the mixture was allowed to react at room temperature for an additional 24 hours.

After the polymer chains were suitably terminated, 0.2 ml of the reaction mixture was added to 1.0 ml of acetonitrile. The ability or inability of acetonitrile to precipitate the polymer was noted (see Table V). The precipitate was collected by centrifugation, washed with acetonitrile, and dried under vacuum. The solid polymer was suspended in 200 μl NMP to afford a concentrated solution, and the qualitative viscosity was noted after two days (see Table V). If a portion of the solid polymer remained insoluble, the amount that entered solution was determined spectrophotometrically (see Table V).

A coating solution was made by adding 80 μl PGMEA and 2.8 μl of 20% Triton X100™ to the concentrated polymer solution. The coating solution was then applied to the surface of a glass slide with a pipette, and the excess allowed to drain by vertically positioning the slide on an absorbent towel. The slide was baked at about 85° C. for two minutes, and at about 110° C. for two minutes. The resulting film was examined microscopically and its characteristics noted (see Table V).

Additional non-alkylated polymers were made using the above methods that afforded Examples 31–43 (see Table V). Each polymer in the series was formed from a diacid chloride mixture and a diamine. The molar ratio of diamine to diacid chlorides was 1.020 (2% molar excess of diamines). The diacid chloride mixture comprised isophthaloyl chloride and terephthaloyl chloride in mole percentages as indicated in Table V. The diamine was either 3,3'-dinitro-4,4'-diaminodiphenyl ether (Examples 30–36), or 2-nitro-p-phenylenediamine (Examples 37–43).

TABLE V

Microscopic Characterization of Representative Polyamides

| Example | mole % isophthaloyl chloride | mole % terephthaloyl chloride | Acetonitrile induced precipitate | Viscosity after two days | Percent soluble | Microscopic characteristics |
|---|---|---|---|---|---|---|
| 30 | 0.0 | 100.0 | yes | 2+; fluidic | 75 | microcrystals |
| 31 | 2.4 | 97.6 | yes | 4+; syrup | 65 | microcrystals |
| 32 | 4.8 | 95.2 | yes | 5+; gel | 50 | microcrystals |
| 33 | 9.1 | 90.9 | Yes | 4+; syrup | 65 | microcrystals |
| 34 | 16.7 | 83.3 | Yes | 2+; fluidic | 75 | microcrystals |
| 35 | 50.0 | 50.0 | None | — | — | — |
| 36 | 100.0 | 0.0 | None | — | — | — |
| 37 | 0.0 | 100.0 | yes | 4+; syrup | 60 | microcrystals |
| 38 | 2.4 | 97.6 | yes | 4+; syrup | 65 | microcrystals |
| 39 | 4.8 | 95.2 | yes | 4+; syrup | 70 | microcrystals |
| 40 | 9.1 | 90.9 | yes | 3+; fluidic | 75 | microcrystals |
| 41 | 16.7 | 83.3 | yes | 2+; fluidic | 90 | microcrystals |
| 42 | 50.0 | 50.0 | yes | 1+; fluidic | 95 | clear |
| 43 | 100.0 | 0.0 | yes | 1+; fluidic | 100 | clear |

As anticipated, the polymer viscosity of Examples 37–43 was inversely related to the meta diacid chloride content in the series. The polymer viscosity of examples 30–36 varied in an unpredicted fashion by increasing, and then decreasing with a peak at about 5% meta diacid chloride content. This polymer series was also unusual in that it manifested a time dependent increase in viscosity, which in Example 32 led to the formation of a gel. The increase in viscosity could be partially reversed by heating, suggesting that the increase was due to non-covalent associations between individual polymer chains. The association between polymers seems to be most favored when a meta turn is placed, on average, at about every $20^{th}$ diacid chloride (i.e., as is seen in Example 32). These changes are consistent with the formation of the nematic phase. As might be anticipated from a model where viscosity is a function of interchain hydrogen-bonding, the solubility of each of the precipitated polymers from Examples 30–43 was inversely related to its viscosity. As shown, the polymers from Examples 35 and 36 had meta diacid chloride contents that precluded precipitation with acetonitrile (i.e., greater than about 50%).

Films made according to Examples 30–34 and 40–43 were further tested for resistance to acetone, acetonitrile, ethanol, and PGMEA. All were found to be resistant. The polymer of example 30 was selected for further alkylation in an effort to avoid the viscosity changes associated with the polymers of Examples 31–34. The polymer of Example 42 was also selected for further alkylation based on its excellent film clarity. A large-scale preparation of each non-alkylated polymer was made using the methods of polymerization disclosed above, but with reagent quantities increased 20-fold. These preparative efforts afforded 11 grams and 34 grams of polymer substantially identical to that obtained from Examples 30 and 42, respectively.

According to an Example 44, alkylation of 100% percent of the amide nitrogens of the polymer from Example 30 was performed by adding 8 grams (0.038 mole of amide nitrogens) of the non-alkylated polymer to 30 ml of NMP. The polymer was initially insoluble and formed a slurry. With the polymer under argon, 0.92 grams (0.038 mole) of sodium hydride in 5 ml NMP was added dropwise. Addition of sodium hydride solubilized the polymer slurry and caused an intense brown-orange coloration, which indicated the formation of a deprotonated amide species. The mixture was stirred for several minutes or until the production of H₂ gas slowed. To this mixture was added 2.49 ml (0.040 mole) of iodomethane, and the mixture was stirred for an additional two hours. The alkylated polymer was then precipitated with 500–800 ml of water and collected by filtration. The collected product was resuspended in 500–800 ml of water as a slurry and filtered. After washing, the polymer was collected and dried under vacuum. One gram of the polymer was then suspended in 5 ml NMP to provide a 20 weight percent stock solution.

The stock solution was used to prepare a liquid photoresist that contained 16 weight percent of the polymer in a solvent mixture comprising 80% NMP, 20% PGMEA, and 0.2% Triton X100™. The photoresist was centrifuged for 5 minutes at 12,000 r.p.m. to remove any microscopic particulates. The photoresist was then applied to the surface of a glass slide with a pipette, and the excess allowed to drain by vertically positioning the slide on an absorbent towel. The substrate was baked at about 85° C. for two minutes, and at about 110° C. for two minutes. The approximately 1 µm thick film was hard, continuous, glassy, and firmly adherent to the slide surface.

The photoresist surface was brought into contact with a mask bearing a 16×16 array of 600 µm×600 µm transparent squares on an opaque background [Precision Image Corporation, Redmond, Wash.]. The transparent squares are separated from one another by 200 µm. The mask was exposed to 365 nm light at an energy density of 8 mW/cm² for 10 minutes using a UV transilluminator [UVP Inc., Upland, Calif.].

With the photoresist appropriately irradiated, the entire substrate was immersed in the developer indicated by Table I. Irradiated photoresist was completely removed from the substrate surface after about 2 to 10 minutes in developer. After development, the entire substrate was rinsed with acetonitrile, air-dried, and baked at about 110° C. for 30 seconds. A fine resolution positive tone relief image was obtained having well defined line spaces. The solvent-resistance of the film was screened against 30 second immersions in acetonitrile, ethanol, cyclohexanone, and toluene. The film was either classified as solvent-resistant or solvent-sensitive depending on the film's integrity after immersion (see Table VI).

The percentage of amide nitrogens alkylated, or "X" in formulas (2) and (3), my be controlled by varying the mole ratio of sodium hydride to polymer amide nitrogen. According to Examples 45–47, the polymer from Example 42 was alkylated at 100, 50, and 20 percent of its amide nitrogens using the above methods. Alkylation of the polymers from Examples 30 and 42 provided photosensitive compositions represented by formulas (2) and (3), respectively. Reagent quantities and polymer yields are summarized in Table VI.

TABLE VI

| Example | NaH (g) | CH₃I (ml) | Yield % | methylated amides, % | characteristics of photopolymer |
|---------|---------|-----------|---------|----------------------|--------------------------------|
| 44 | 0.92 | 2.49 | 55 | 100 | solvent resistant, imageable |
| 45 | 1.35 | 4.05 | 49 | 100 | solvent sensitive |
| 46 | 0.68 | 2.02 | 80 | 50 | solvent resistant, imageable |
| 47 | 0.27 | 0.81 | 77 | 20 | solvent resistant, imageable |

As shown by Example 44, the photosensitive composition represented by formula (2) remains imageable and solvent resistant with up to 100 mole percent of amide nitrogens alkylated. In contrast, Examples 45–47 demonstrate that the photosensitive composition represented by formula (3) becomes solvent sensitive when the percentage of alkylated amide nitrogens is greater than about 50 mole percent. The clarity of the films was excellent with no microcrystal formation as seen in many of the unalkylated polymers in Table V. All the films were readily stripped by immersion in NMP.

From the foregoing, it will be appreciated that, although specific embodiments of the invention have been described herein for the purpose of illustration, various modifications may be made without deviating from the spirit and scope of the invention. Accordingly, the present invention is not limited except by the appended claims.

What is claimed is:

1. A photoactive polyamide derivative comprising a plurality of repeating units represented by the formula:

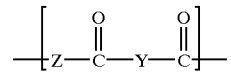

wherein Z in 20 to 50 percent of the plurality of repeating units comprises a divalent radical represented by the formula:

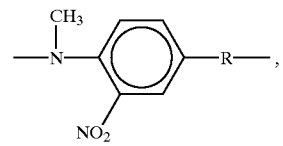

wherein R is a divalent radical;

wherein Z in the balance of the plurality of repeating units comprises a divalent radical represented by the formula:

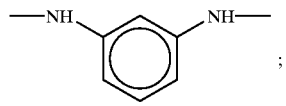

and wherein Y in 10 to 100 percent of the plurality of repeating units comprises an isophthaloyl radical, and Y in the balance of the plurality of repeating units comprises a terephthaloyl radical.

2. A photoactive polyamide derivative according to claim 1, wherein R is a divalent radical represented by one of the formulas:

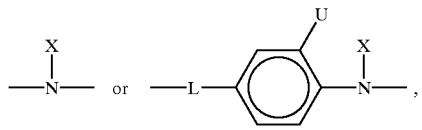

wherein X is H or CH₃; L is selected from the group consisting of direct link, O, CH₂, N(CH₃), C(CH₃)₂, C(CF₃)₂, SO₂, CO, CONH, O(C₆H₄)₂, S, C(C₆H₅)₂ and C(CF₃)(C₆H₅); and U is selected from the group consisting of H, NO₂ and CH₃.

3. A photoactive polyamide derivative according to claim 1, wherein R is NH.

4. A photoactive polyamide derivative according to claim 1, wherein the polyamide derivative has a number average degree of polymerization that is greater than 15.

5. A photoactive polyamide derivative according to claim 1, wherein the polyamide derivative has a number average degree of polymerization that is greater than 20.

6. A photoactive polyamide derivative according to claim 1, wherein the polyamide derivative has a number average degree of polymerization that is greater than 50.

7. A photoactive polyamide derivative according to claim 1, wherein the polyamide derivative has a number average degree of polymerization that is greater than 100.

8. A photoactive polyamide derivative according to claim 1, wherein the polyamide derivative is terminated by a monovalent organic group.

9. A photoactive polyamide derivative according to claim 8, wherein the monovalent organic group is represented by one of the formulas:

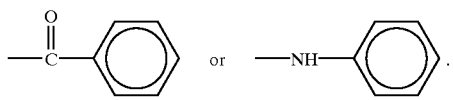

10. A photosensitive resin composition, comprising a photoactive polyamide derivative according to claim 1, in combination with a solvent.

11. A composition according to claim 10, further comprising a photoinactive polyamide, wherein the photoactive polyamide derivative and the photoinactive polyamide are combined to form a substantially homogeneous blend.

12. A composition according to claim 11, wherein the photoinactive polyamide is formed by the condensation of meta-phenylenediamine with isophthaloyl chloride and terephthaloyl chloride.

13. A photoactive polyamide derivative that is the product of the condensation of a diamine mixture with a diacid chloride mixture, wherein the diamine mixture comprises 20 to 50 mole percent of $N^1$-methyl-2-nitro-p-phenylenedine, with the balance cons essentially of 1,3-phenlyenediamine, and wherein the diacid chloride mixture comprises 10 to 100 mole percent of isophthaloyl, with the balance consisting essentially of terephthaloyl chloride.

14. A photoactive polyamide derivative that is the product of the condensation of a diacid chloride mixture with a diamine mixture, wherein the diacid chloride mixture comprises 10 to 100 mole percent of isophthaloyl chloride, with the balance consisting essentially of terephthaloyl chloride, and wherein the diamine mixture comprises 20 to 50 mole percent of an N-alkyl-2-nitro diamine, with the balance consisting essentially of 1,3-phenylenediamine, wherein the N-alkyl-2-nitro diamine is:

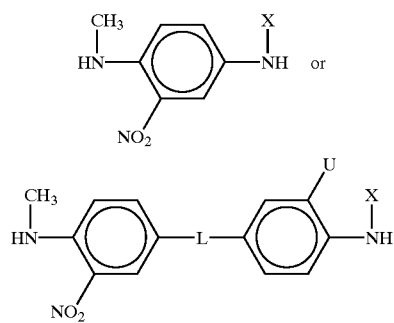

wherein X is H or $CH_3$; L is selected from the group consisting of direct link, O, $CH_2$, $N(CH_3)$, $C(CH_3)_2$, $C(CF_3)_2$, $SO_2$, CO, CONH, $O(C_6H_4)_2$, S, $C(C_6H_5)_2$, and $C(CF_3)(C_6H_5)$; and U is selected from the group consisting of H, $NO_2$ and $CH_3$.

15. A photoactive polyamide derivative according to claim 14, wherein the N-alkyl-2-nitro diamine is 3,3'-dinitro-4,4'-di-N-methylaminodiphenyl ether.

16. A photoactive polyamide derivative according to claim 14, wherein the mole ratio of the diacid chloride mixture to the diamine mixture ranges from 0.909 to 1.100.

17. A photoactive polyamide derivative according to claim 14, wherein the mole ratio of the diacid chloride mixture to the diamine mixture ranges from 0.980 to 1.020.

18. A photoactive polyamide derivative according to claim 14, wherein the diacid chloride mixture condenses with at least 80% of the N-alkyl-2-nitro diamine before condensing with the 1,3-phenylenediamine.

19. A photoactive polyamide derivative according to claim 14, wherein the polyamide derivative is terminated with benzoyl chloride.

20. A photoactive polyamide derivative according to claim 14, wherein the polyamide derivative is terminated with aniline.

21. A photosensitive composition, comprising a photoactive polyamide derivative according to claim 14, in combination with a solvent.

22. A photosensitive composition comprising a photoactive polyamde derivative that is the product of the condensation of a diacid chloride mixture with a diamine mixture, wherein the diacid chloride mixture comprises 10 to 100 mole percent of isophthaloyl chloride, with the balance consisting essentially of terephthaloyl chloride, and wherein the diarine mixture comprises 50 to 100 mole percent of the N-alkyl-2-nitro diaine with the balance consisting essentially of 1,3-phenylenediame, wherein the N-alkyl-2-nitro diamine is:

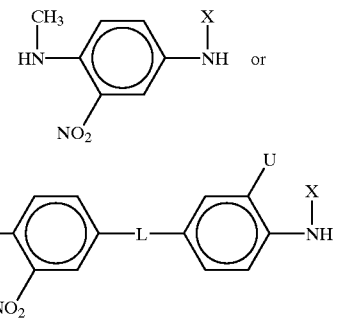

wherein X is H or $CH_3$; L is selected from the group consisting of direct link, O, $CH_2$, $N(CH_3)$, $C(CH_3)_2$, $C(CF_3)_2$, $SO_2$, CO, CONH, $O(C_6H_4)_2$, S, $C(C_6H_5)_2$, and $C(CF_3)(C_6H_5)$; and U is selected from the group consisting of H, $NO_2$ and $CH_3$ in combination with a solvent and further comprising a photoinactive polyamide that is the product of condensing meta-phenyl dia e with isophthaloyl chloride and terephthaloyl chloride.

23. A photoactive polyamide derivative comprising a plurality of repeating units represented by the general formula:

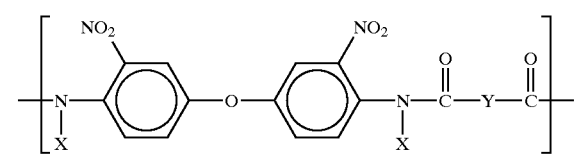

wherein 10 to 100 percent of X radicals are methyl radicals, and wherein the balance of X radicals are H radicals;

and wherein 0 to 50 percent of Y radicals are isophthaloyl radicals, with the balance of Y radicals terephthaloyl radicals.

24. A photoactive polyamide according to claim 23, wherein the polyamide derivative has a number average degree of polymerization that is greater than 15.

25. A photoactive polyamide according to claim 23, wherein the polyamide derivative has a number average degree of polymerization that is greater than 20.

26. A photoactive polyamide according to claim 23, wherein the polyamide derivative has a number average degree of polymerization that is greater than 50.

27. A photoactive polyamide according to claim 23, wherein the polyamide derivative has a number average degree of polymerization that is greater than 100.

28. A photoactive polyamide according to claim 23, wherein the polyamide derivative is terminated by a monovalent organic group.

29. A photoactive polyamide according to claim 28, wherein the monovalent organic group is represented by one of the formulas:

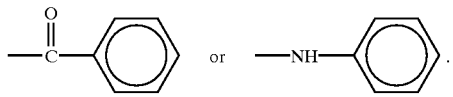

30. A photosensitive composition, comprising a photoactive polyamide derivative according to claim 23, in combination with a solvent.

31. A method of producing a photoactive polyamide, comprising the sequential steps of:
(a) condensing a diacid chloride mixture with 3,3'-dinitro-4,4'-diamnodiphenyl ether to form a photoinactive polyamide, wherein the diacid chloride mixture comprises from 0 to 50 mole percent of isophthaloyl chloride, with the balance consisting essentially of terephthaloyl chloride; and
(b) alkylating the photoinactive polyamide with methyl radicals at 10 to 100 mole percent of amide nitrogens; and therefrom generating a photoactive polyamide.

32. A method according to claim 31, wherein the mole ratio of the diacid chloride mixture to 3,3'-dinitro-4,4'-diaminodiphenyl ether ranges from 0.909 to 1.100.

33. A method according to claim 31, wherein the mole ratio of the diacid chloride mixture to 3,3'-dinitro-4,4'-diaminodiphenyl ether ranges from 0.980 to 1.020.

34. A method according to claim 31, wherein the photoinactive polyamide is terminated with benzoyl chloride.

35. A method according to claim 31, wherein the photoinactive polyamide is terminated with aniline.

36. A photoactive polyamide derivative having a plurality of repeating units represented by the general formula:

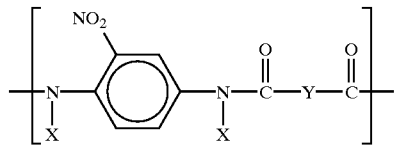

wherein 10 to 50 percent of X radicals are methyl radicals and the balance of X radicals are H radicals, and wherein 20 to 100 percent of Y radicals are isophthaloyl radicals, and the balance of Y radicals are terephthaloyl radicals.

37. A photoactive polyamide derivative according to claim 36, wherein the polyamide derivative has a number average degree of polymerization that is greater than 15.

38. A photoactive polyamide derivative according to claim 36, wherein the polyamide derivative has a number average degree of polymerization that is greater than 20.

39. A photoactive polyamide derivative according to claim 36, wherein the polyamide derivative has a number average degree of polymerization that is greater than 50.

40. A photoactive polyamide derivative according to claim 36, wherein the polyamide derivative has a number average degree of polymerization that is greater than 100.

41. A photoactive polyamide derivative according to claim 36, wherein the polyamide derivative is terminated by a monovalent organic group.

42. A photoactive polyamide derivative according to claim 41, wherein the monovalent organic group is represented by one of the formulas:

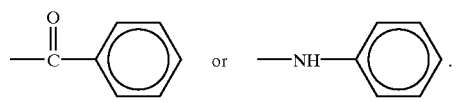

43. A photosensitive composition, comprising a photoactive polyamide derivative according to claim 36, in combination with a solvent.

44. A method of producing a photoactive polyamide, comprising the sequential steps of:
(a) condensing a diacid chloride mixture with 2-nitro-p-phenylenediamine to form a photoinactive polyanide, wherein the diacid chloride mixture comprises from 0 to 50 mole percent of isophthaloyl chloride, with the balance consisting essentially of terephthaloyl chloride; and
(b) alkylating the photoinactive polyamide with methyl radicals at 10 to 100 mole percent of amide nitrogens; and therefrom generating a photoactive polyamide.

45. A method according to claim 44, wherein the mole ratio of the diacid chloride mixture to 2-nitro-p-phenlyenediamine is ranges from 0.909 to 1.100.

46. A method according to claim 44, wherein the mole ratio of the diacid chloride mixture to 2-nitro-p-phenylenediamine is in the range of 0.980 to 1.020.

47. A method according to claim 44, wherein the photoinactive polyamide is terminated with benzoyl chloride.

48. A method according to claim 44, wherein the photoinactive polyamide is terminated with aniline.

* * * * *

UNITED STATES PATENT AND TRADEMARK OFFICE
CERTIFICATE OF CORRECTION

| | | |
|---|---|---|
| PATENT NO. | : 6,569,598 B2 | Page 1 of 1 |
| APPLICATION NO. | : 09/836929 | |
| DATED | : May 27, 2003 | |
| INVENTOR(S) | : John A. Zebala | |

It is certified that error appears in the above-identified patent and that said Letters Patent is hereby corrected as shown below:

Col. 1, line 19.
Insert a Government Rights Statement as shown below:

--This invention was made with government support under Grant Number DAMD17-96-1-6120 awarded by the U.S. Army Medical Research and Materiel Command. The government has certain rights to this invention.--

Signed and Sealed this
Eighteenth Day of December, 2012

David J. Kappos
*Director of the United States Patent and Trademark Office*